United States Patent [19]

Ischinger et al.

[11] Patent Number: 5,131,407
[45] Date of Patent: Jul. 21, 1992

[54] GUIDEWIRE WITH TRACKING MEMBER AND CATHETER EXCHANGE SYSTEM

[75] Inventors: Thomas A. Ischinger, Munich, Fed. Rep. of Germany; Thomas J. Palermo, Methuen, Mass.

[73] Assignee: C. R. Bard, Inc., Murray Hill, N.J.

[21] Appl. No.: 700,104

[22] Filed: May 8, 1991

Related U.S. Application Data

[63] Continuation of Ser. No. 444,516, Dec. 1, 1989.

[51] Int. Cl.$^5$ .................................. A61M 25/00
[52] U.S. Cl. ........................... 128/772; 128/657; 604/282
[58] Field of Search ............. 128/657, 772; 604/95, 604/164, 170, 280, 282, 264

[56] References Cited

U.S. PATENT DOCUMENTS

| | | | |
|---|---|---|---|
| 4,719,924 | 1/1988 | Crittenden et al. | 128/772 |
| 4,748,982 | 6/1988 | Horzewski et al. | 128/344 |
| 4,757,827 | 7/1988 | Buchbinder et al. | 128/772 |
| 4,762,129 | 8/1988 | Bonzel | 128/344 |
| 4,771,782 | 9/1988 | Millar | 128/637 |
| 4,824,435 | 4/1989 | Giesy et al. | 128/772 |
| 4,875,489 | 10/1989 | Messner | 128/657 |
| 4,932,413 | 6/1990 | Shockey et al. | 128/657 |
| 4,953,553 | 9/1990 | Tremulis | 128/772 |

*Primary Examiner*—Randy C. Shay
*Attorney, Agent, or Firm*—Wolf, Greenfield & Sacks

[57] ABSTRACT

A guidewire and method of using same for tracking an indwelling device such as a catheter previously positioned within a body lumen. The guidewire includes an elongate flexible body shaft having proximal and distal ends, and a tracking member disposed at the region of the distal end. The tracking member defines an opening passable over the shaft of the indwelling device. During use, the tracking member is slid along the indwelling device toward its distal end to enable the guidewire to track the path of the indwelling device. The indwelling device then may be withdrawn from the patient's body lumen and an over-the-wire catheter may be threaded onto and advanced along the guidewire into the patient's body lumen. The tracking member is retractable within and removable from the guidewire. The invention is useful particularly in catheterization procedures where it is desired to exchange an over-the-wire catheter for a catheter having a fixed or integral guidewire.

30 Claims, 4 Drawing Sheets

GUIDEWIRE WITH TRACKING MEMBER AND CATHETER EXCHANGE SYSTEM

This application is a continuation of application Ser. No. 444,516, filed Dec. 1, 1989.

FIELD OF INVENTION

This invention relates to guidewires for guiding catheters through a patient's blood vessels and an improvement in performing catheter exchanges using such guidewires.

BACKGROUND OF THE INVENTION

This invention concerns improvements in the use of small diameter low profile dilatation catheters used to dilate an obstructed artery such as in angioplasty and, particularly, coronary angioplasty. In performing coronary angioplasty, it often occurs that the physican may wish to use a catheter different than the one originally inserted into the patient. For example, this may occur if the initial selection of catheter balloon size was inappropriate to treat the obstruction (stenosis) or if some other event occurs that would make the use of a different catheter desirable. When the catheter is of the type that uses a separate movable guidewire, for example, as disclosed in U.S. Pat. No. 4,545,390 (Leary), the catheter may be exchanged in a well-known procedure in which an exchange wire is substituted for the movable guidewire (or the length of the guidewire is extended with an extension wire); then the catheter is withdrawn over the exchange wire and the replacement catheter is threaded over the exchange wire and is thereby guided to the stenosis. By maintaining the guidewire in position in the stenosis during the exchange procedure, the replacement catheter is easily and quickly advanced to the stenosis.

The foregoing catheter exchange procedure is not usable with small diameter low profile dilatation catheters of the type that incorporate an integral guidewire because the balloon catheter cannot be separated from the guidewire. Thus, when it is desired to exchange such a fixed wire dilatation catheter for another catheter, such as a catheter utilizing a movable guidewire, the procedure has required withdrawal of the entire fixed wire catheter. Withdrawal of the fixed wire catheter, however, results in loss of position of the catheter in the stenosis. Consequently, there is nothing in the patient's blood vessel to guide the succeeding catheter to the stenosis. As a result, a new guidewire must be inserted and remanipulated through the patient's arterial system to reach and then cross through the stenosis, thereby to provide a guiding path over which the succeeding balloon catheter can be advanced. The replacement of a integral fixed wire catheter with a guidewire necessarily involves time consuming manipulation and steering of the guidewire to advance it to and through the stenosis. The additional procedure increases the risk to the patient.

It would be desirable, therefore, to provide a means by which catheter exchanges involving a small diameter low profile dilatation catheter having an integral guidewire could be effected easily, quickly, without loss of position and with minimal trauma. It is among the objects of the invention, to provide such a system and, particularly, to provide a guidewire that can be guided to the stenosis by the fixed wire dilatation catheter.

SUMMARY OF THE INVENTION

In the present invention, a guidewire is provided with a tracking member at its distal end, in the form of a relatively large diameter loop, which can be looped over the indwelling catheter. The guidewire then can be advanced into the patient's vasculature and will follow the path of the indwelling catheter directly to the site of the stenosis and into and through the stenosis. With the guidewire positioned in the stenosis, the indwelling catheter can be removed. The tracking member and guidewire are constructed so that the looped tracking member can be retracted into the guidewire. The guidewire then can serve its normal function of providing a path to guide the succeeding catheter directly to the stenosis to be treated.

The guidewire includes an elongate tubular metal shaft, an intermediate tubular plastic sleeve connected to the distal end of the tubular shaft, and a helical coil spring connected to the distal end of the tubular sleeve. A core wire is sewed to the distal end of the metal shaft and extends within the plastic sleeve to the distal end of the coil spring.

The tracking member may be in the form of a helical coil of enlarged diameter that surrounds the smaller diameter coil spring on the guidewire. The wire that forms the helical coil is attached to an elongate pull wire that passes into the guidewire between a pair of spaced coils of the coil spring and through the plastic tube, into the metal tubular shaft and out of the proximal end of the shaft. The helically coiled tracking member can be withdrawn into the guidewire by pulling on the proximal end of the pull wire. The indwelling fixed wire catheter then can be withdrawn from the patient.

After the guidewire has been advanced and its distal end positioned in the stenosis, and after the previous indwelling catheter has been withdrawn, a guidewire extension is attached to the proximal end of the guidewire in order that some portion of the guidewire extension or guidewire will be exposed as the succeeding catheter is advanced over the guidewire. It is necessary for some portion of the guidewire or guidewire extension to be exposed so that it may be gripped by the physician or an assistant in order to prevent the advancing catheter from frictionally dragging the guidewire further into the blood vessel together with the catheter.

It is among the objects of the invention to provide a new guidewire and technique for positioning a guidewire by tracking a previously installed device.

Another object of the invention is to provide a guidewire that may be advanced along side and guided by an indwelling catheter directly to a stenosis so that the indwelling device may be removed, thus leaving the guidewire in place and in readiness to guide an over-the-wire catheter to the site of the stenosis.

A further object of the invention is to provide an improved device and system for effecting exchange of a low profile catheter having an integral guidewire for an over-the-wire catheter adapted to be passed over a separate, movable guidewire.

Another object of the invention is to provide a guidewire having monorail-like tracking element at its distal end that can be retracted while the guidewire remains in the patient.

A further object of the invention is to provide such a guidewire and method of using same which reduce the number of steps involved in accomplishing exchange of a fixed guidewire catheter.

DESCRIPTION OF THE DRAWINGS

The foregoing and other objects and advantages of the invention will be appreciated more fully from the following further description thereof with reference to the accompanying drawings wherein.

DESCRIPTION OF THE ILLUSTRATIVE EMBODIMENT

According to the invention a guidewire is provided for tracking an indwelling device, such as a previously placed catheter. In the illustrative embodiment an elongate flexible guidewire is provided with a tracking member disposed at the distal region of the guidewire. The tracking member defines an enlarged loop that can be placed over the exposed proximal end of the indwelling device so that the tracking member may be slid along and follow the path of the indwelling device. After the guidewire has been advanced to the intended site in the patient's body, the tracking member may be retracted into the guidewire and the indwelling catheter may be removed. Another catheter then can be advanced over the proximal end of the guidewire and along the guidewire to the intended vascular or other site. A preferred guidewire is indicated generally at 10 in FIG. 1A. The guidewire 10 has a proximal end (toward the left in FIG. 1A) and a distal end (to the right in FIG. 1A). A tracking member, indicated generally at the numberal 12, is disposed at the distal region of the guidewire. The tracking member 12 is both fully retractable, and removable from the guidewire 10. The tracking member 12 defines an enlarged loop-like element in which the loop extends transversely of the guidewire to an extent sufficient to enable the tracking member 12 to be passed over a catheter, indicated in phantom at 14.

Figures 1A, 1B, 2:
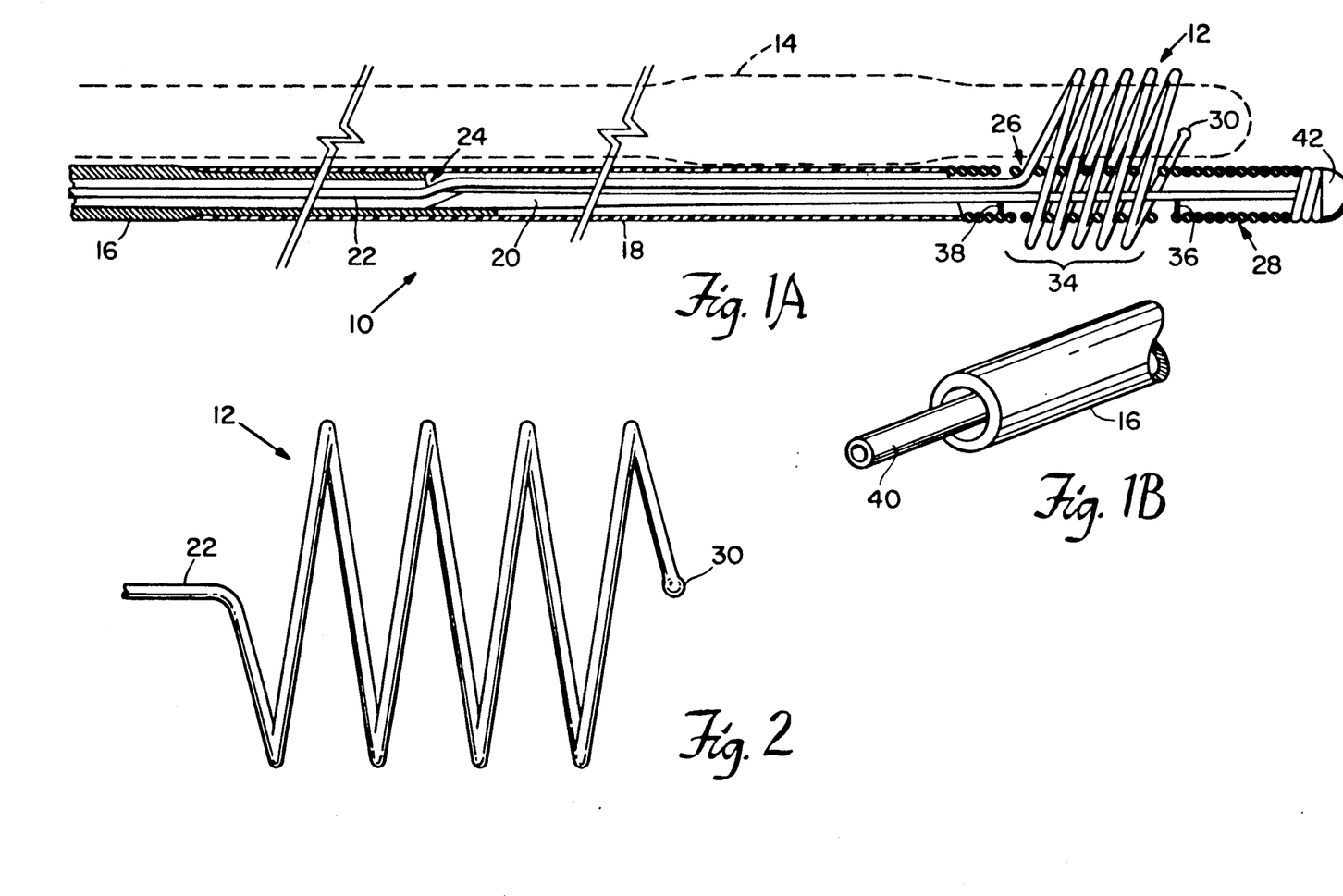
FIG. 1A is a somewhat diagrammatic, fragmented, section illustration of the distal portion of a guidewire of the invention with a tracking member passing over an indwelling catheter which is suggested in phantom.
FIG. 1B is a perspective view of the proximal end of the guidewire of FIG. 1A showing the portion of the pull wire of the tracking member emerging from the proximal end of the guidewire.
FIG. 2 is an enlarged, more detailed view of the coils of the tracking member of FIG. 1A.
Figure 1C:
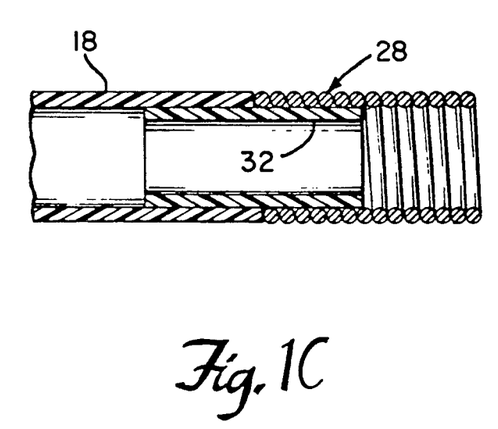
FIG. 1C is a sectional illustration of the juncture of the polyimide tube and the helical coil of the guidewire.

The guidewire 10 includes an elongate tubular shaft 16 formed of stainless steel hypodermic tubing, the distal end of which may be connected to a flexible polyimide sleeve 18. The proximal end of the sleeve 18 overlaps the distal end of the shaft 16 by approximately two centimeters and may be secured by adhesive such as cyanoacrylate, available from the Loctite Corporation. The proximal end of a core wire 20 preferably is attached, as by soldering, to the distal end of the hypodermic tubing 16. Attached to and extending distally of the plastic sleeve 18 is an elongate flexible helical coil 28 which terminates, at its distal tip, at a rounded tip weld 42. The core wire 20 extends through the helical coil 28 and is attached, either directly or through a safety ribbon, as is well-known, to the tip weld 42. The core wire 20 is tapered in a distal direction to provide for increasing flexibility of the guidewire in a distal direction. The taper may be continuous or may be in the form of a stepped taper. As seen in FIG. 1C, the proximal end of the coil spring 28 is connected to the distal end of the sleeve 18 by a 0.5 cm polyimide tubular insert 32 which extends approximately 2.5 mm inside of the respective ends of the sleeve 18 and the coil spring 28. The respective ends are secured to the insert 32 by adhesive such as Loctite.

The tracking member 12 is on the distal portion of a metal wire 22 which extends proximally through the sleeve 18 and enters the lumen of the tubular shaft 16 through a slot 24 found in the tubluar shaft just proximally of the connection of the core wire 20 to the shaft 16. The distal end of the wire 22 emerges through a gap 26 in the coils of helical coil spring 28 and forms a plurality of enlarged helical loops about the coil spring 28. The distal tip 30 of the wire 22 terminates in a free, unattached end which enables the entire wire 22 to be retracted into and detached from the guidewire 10, as described in more detail below.

An expanded region 34 of the coil spring 28 is established by securely attaching the ends of the stretched region 34 to the core wire 20. The attachment may be by a distal braze 36 and a proximal braze 38, each of which is attached to the distal portion of the core wire 20 after the coils within the expanded region 34 are stretched apart. In order to permit withdrawal of the wire 22, it is important that at least the proximal braze 38 does not completely fill the interior of the coil spring 28. The braze joint 38 thus does not completely encircle the core wire 20, but instead allows the wire 22 to be drawn past it. Preferably, the expanded region 34 is at least as long as the length of the helical coils of the tracking member 12 so that the helically coiled tracking member 12 can be displaced laterally to one side of the guide wire coil 28 and be enmeshed with the expanded coils and against the core wire 20. The lateral shifting of the tracking member loops provides a greater effective inner diameter for the tracking member in which to receive the indwelling catheter 14. It also inhibits longitudinal movement of the tracking loops relative to the guidewire 10 by interlocking them.

In one embodiment, adapted for use in percutaneous transluminal coronary angioplasty (PTCA) the guidewire 10 has an overall length of approximately 185 cm. The tubular shaft 16 is approximately 150 cm in length and, by way of example, may have an outer diameter of 0.016 inch and an inner diameter of 0.009 inch. The plastic tubular sleeve 18 may be approximately 30 to 32 cm in length, having an outer diameter of 0.0155 inch and an inner diameter of 0.014 inch. Such polyimide tubing is commerically available from Polymicro, Inc. of Scottsdale, Arizona. The core wire 20 is a tapered stainless steel wire approximately 32 to 34 cm in length. The coil spring 28 is formed of 0.002 inch diameter platinum alloy wire, such as 92% platinum and 8% tungsten and may be wound to have an outer diameter of 0.016 inch, an inner diameter of 0.012 inch, and a length of 3 cm. The tracking member 12 may be formed from 0.003 inch diameter wire made of an alloy of 10% nickel and 90% platinum which is wound to form tracking member loops having a total length of approximately 0.75–1.0 cm, an outer diameter of between 0.042–0.048 inch and an inner diameter of between 0.039–0.045 inch. The alloy is radiopaque which assists in monitoring of the guidewire 10 using fluoroscopy. Additionally it has good resilience and tensile strength. Such wire, which is heat treated by the manufacturer so that it will be straight when taken off the supply spool is commercially available from Sigmund Cohn Corporation of New York.

In order to enable the helical coil of the tracking member 12 to be retracted into the guidewire the tracking member wire 22 is connected at its proximal end to an elongate proximal pulling element 40 which emerges through the proximal end of the tubular shaft 16 as shown in FIG. 1B. The proximal end of the wire 22 and the distal end of the proximal pulling element 40 may be connected with an appropriate adhesive such as cyanoacrylate adhesive available from the Loctite Corporation. In order to facilitate assembly of the device, it is preferred to form the pulling element 40 from a material that will display suitable compressive column strength when in a relatively small diameter as is necessary to pass through the guidewire. A preferred material for the element 40 is a silica glass hypotube approximately 150 cm in length and having an outer diameter of 0.006 inch and an inner diameter of 0.0035 inch. Such a glass hypotube is available from Polymicro, Inc. The silica glass hypotube 40 is preferably coated with a polyimide to provide a low friction surface. Friction may further be decreased for both the coated hypotude 40 and the polyimide sleeve 18 by coating or imbedding the polyimide with Teflon. In order to assemble the tracking member 12 and associated pulling elements with the guidewire, the elongate element 40 is inserted into the tubular shaft 16 at its proximal end and is pushed through the lumen of the tubular shaft 16, through the opening 24 at the distal end of the tubular shaft 16, through the plastic tubing 18 and into and out of the coil spring 28, emerging from a space 26 in the region 34 of the space spring coils. It may be noted that the proximal end of the core wire adjacent opening 24 is inclined to aid in guiding the distal end of the glass tube 40 when it is inserted into the guidewire. With the distal end of the silica glass hypotube 40 so exposed, it is adhesively attached to the proximal end of the tracking member wire 22 which may be inserted into the lumen of tube 40. After attachment, the pulling element 40 is drawn proximally through the guidewire, drawing the tracking member 22 proximally and about the distal portion of the guidewire, as illustrated in FIG. 1A. It should be understood that the use of a glass tube for the pulling element 40 is preferred because it displays greater column strength than the nickel platinum material of the wire 22 in a diameter of about 0.006" and, therefore, is more resistant to kinking and is more readily pushed through the guidewire during the assembly procedure.

In an alternate arrangement for connecting the tracking member 12 to the proximal pulling element 40 (illustrated in FIG. 5), an intermediate, thin ribbon-like intermediate wire 35 may be interposed between the distal end of the pulling element 40 and the proximal end of the wire 22, the lengths of the wire 22 and pulling element 40 being appropriately adjusted to accept the intermediate wire. Preferably, the ribbon wire is about 35 to 40 cm in length and has a rectangular cross-section of 0.001"×0.003".

Figure 5:
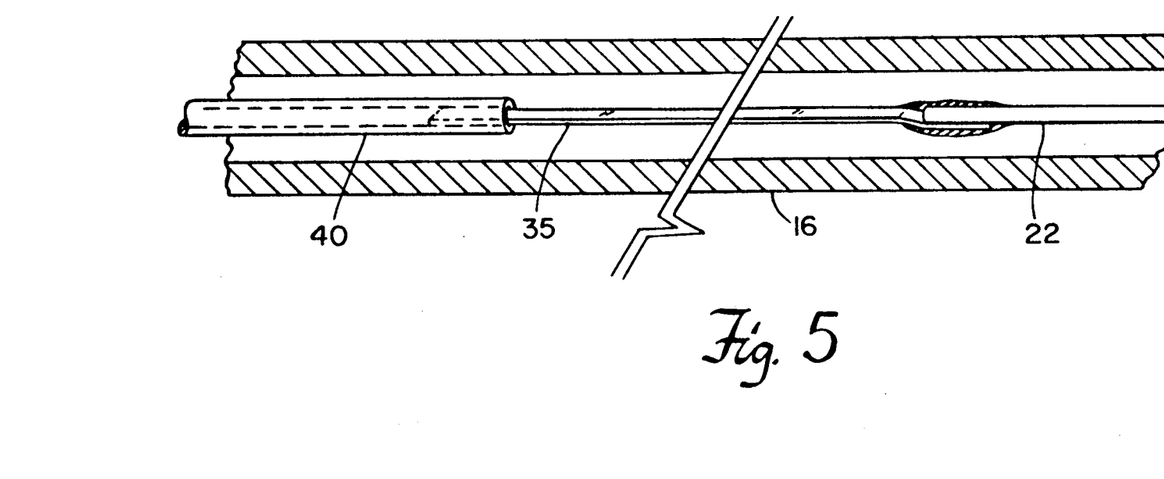
FIG. 5 illustrates a portion of the pull wire arrangement.

In the assembly of this embodiment the proximal end of the ribbon wire 35 is inserted within the distal end of the glass silica hypotube 40 and secured with adhesive, and the assembly is advanced distally through the shaft 16 until the distal end of the ribbon passes through the slot 24. The ribbon wire 35 is advanced through the sleeve 18 until the opening 26 in the coil spring 28 is reached. The end of the wire 35 then is drawn through the opening 26 to expose the distal end of the ribbon wire 35 to the exterior of the guidewire 10. The nickel platinum wire 22 then is provided, having the tracking member loops 12 previously formed at its distal end and having a proximal straight section approximately by 34–40 cm in length. The proximal end of the straight section is connected to the distal end of the ribbon wire by brazing. The foregoing alternate technique of assembly may be met if there is difficulty in drawing the glass tube 40 through the opening 24, as described above. In either case, after the wire 22 is secured, the glass hypotube 40 is pulled proximally to draw the wire 22 within the sleeve 18 and through the slot 24 into the main wire 16. The tracking member 12 is guided over the distal tip bead 42 of the wire 10 until it is centered over the expanded region 34 which is approximately 1 cm in length.

It is desirable to provide a spherical bead for the tip 30 of the wire 22. The blunt tip 30 acts as a safety feature to avoid possible perforation of a blood vessel wall. The blunt tip 30 is formed by heating the nickel platinum alloy using a plasma weld, or attaching a separate material such as solder. The tip 40 preferably has an outer diameter of 0.005–0.006 inch.

Figures 3A, 3B, 3C, 3D:
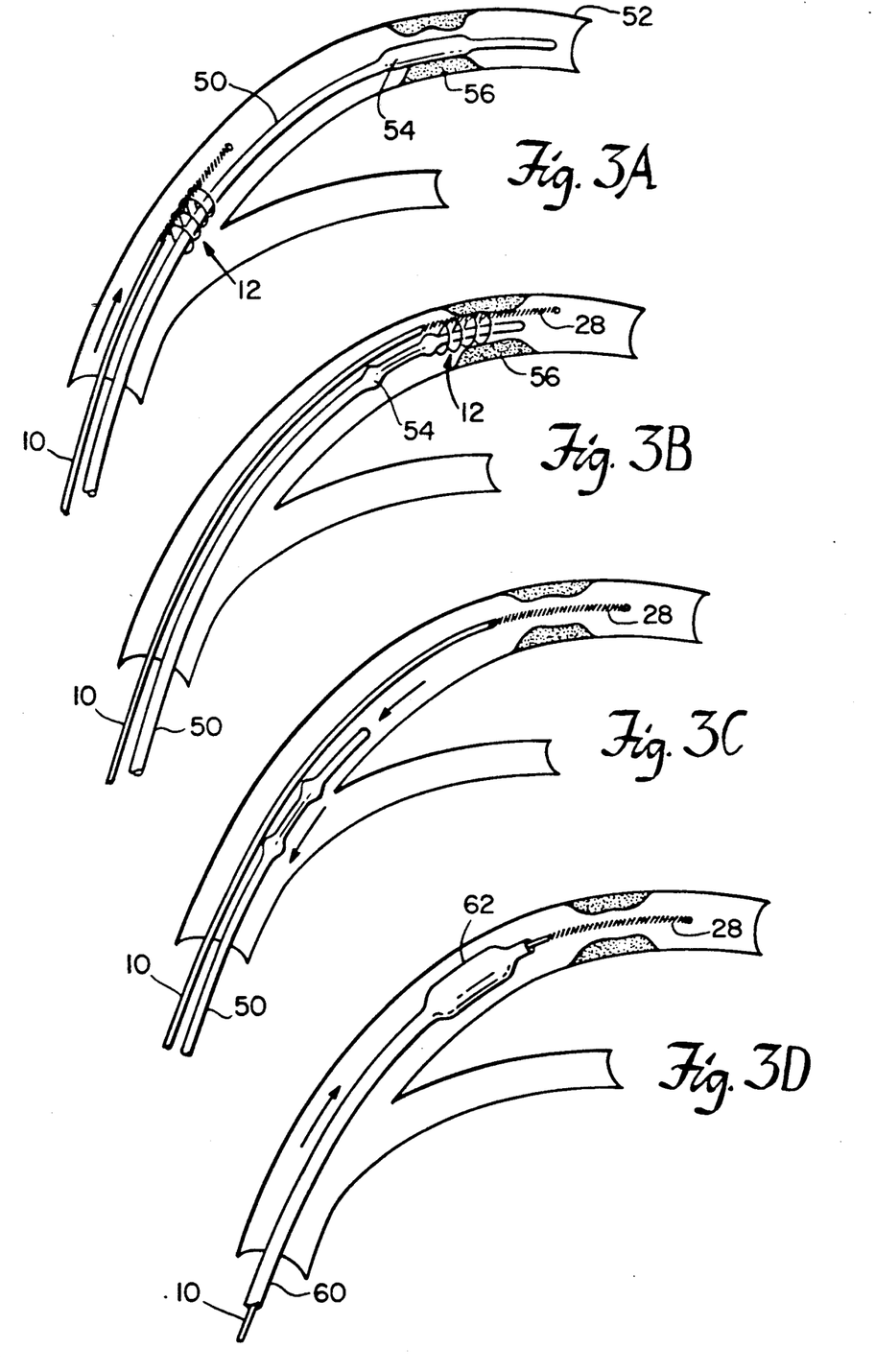
FIG. 3A is a schematic representaton of a guidewire according to the invention tracking an indwelling catheter positioned across a stenosis.
FIG. 3B shows the guidewire passing across the stenosis.
FIG. 3C shows removal of the indwelling device and contraction of the tracking member.
FIG. 3D is a schematic view of the succeeding, over-the-wire balloon catheter being advanced along the guidewire toward the stenosis.
Figure 4:
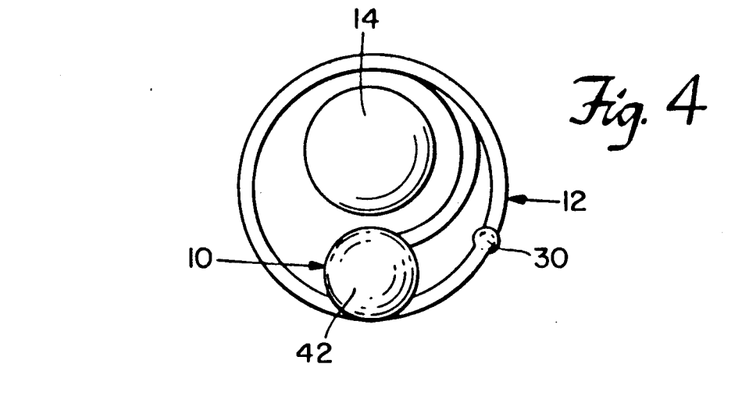
FIG. 4 is an end view of the guidewire with the tracking member in a transversely shifted position with the indwelling catheter extending through the tracking member.

A technique of using a guidewire according to the invention is shown in FIGS. 3A–3D. A catheter 14, such as a low profile catheter having a fixed, or integral guidewire is shown as having been previously advanced and manipulated into position within a selected blood vessel branch 52. The dilatation balloon 54 of the catheter is shown as positioned in a stenosis 56 which was previously dilatated by the balloon 54. Should it be desired to exchanged the catheter 50 for an over-the-wire type of catheter the tracking member 12 is attached to the proximal end of the catheter that is exposed exteriorly of the patient. The proximal end of the indwelling catheter 14 typically will have an enlarged hub that cannot be passed axially through the loop defined by the tracking member 12 even when the tracking member 12 has been shifted sideways to its most lateral position relative to the guidewire 10. The tracking member 12 is attached to the indwelling catheter at a location distally of the proximal fitting of the indwelling catheter by inserting and crossing the shaft of the indwelling catheter transversely between a pair of adjacent coils of the tracking member 12 and rotating the tracking member 12. The rotation of the tracking member may be effected by rotating the entire assembly of the guidewire and tracking member 12. By maintaining the distal tip of the coil of the tracking member free and unattached, the tracking member 12 can be manipulated with respect to the indwelling catheter shaft to dispose the entire helical coil of the tracking member about the indwelling catheter shaft. The guidewire 10 is then advanced into the blood vessel, with tracking member 12 sliding along the catheter 14 to track the path of the microcatheter 14. The ballon 54 is deflated as shown in FIG. 3B and tracking member 12 is advanced over the ballon to pass the coil spring 28 through the stenosis 56. The catheter 14 is then withdrawn, FIG. 3C, and the tracking member 12 is retracted within the guidewire 10 by pulling on the proximal element 40, FIG. 1B. As the helically coiled tracking element 12 is pulled into the lumen of the guidewire 10, it uncoils to a more straightened configuration in which it can be pulled through and out of the guidewire, thus leaving the guidewire in place and in readiness to guide a succeeding over-the-wire catheter 60 having a dilatation balloon (or other means for performing an angioplasty) as shown in FIG. 3D. It should be noted that in order to advance the succeeding catheter 60 over the guidewire 10 while maintaining position of the distal end of the guidewire in the stenosis, the proximal end of the guidewire that extends exteriorly of the patient, should be extended in length. The exteriorly exposed extended length of the guidewire should be longer than the length of the over-the-wire catheter that is to be successively placed in the patient. The extra length of the extended guidewire assures that some portion of the guidewire (or its extension) will be exposed and grippable by the physician or an assistant while the catheter is advance over the wire. That is necessary to prevent the advancing catheter from frictionally dragging the guidewire further distally into the patient's blood vessel. A guidewire extension system suitable for use with the present invention is disclosed in detail in U.S. Patent application Ser. No. 206,008, filed Jun. 13, 1988 to which reference is made for a complete detailed description thereof, the disclosure of application Ser. No. 206,008 being hereby incorporated by reference in its entirety. It is noted that the guidewire extension system described in application Ser. No. 206,008 includes an extension wire which is intended to be inserted into a tubular socket at the proximal end of the guidewire. In the present invention, the proximal end of the guidewire, as illustrated in FIG. 1B, is tubular and defines such a socket adapted to receive an extension wire.

In addition to the foregoing the guidewire with attached enlarged coil 12 may be used as a temporary or emergency stent to maintain patent an artery which, after an angioplasty procedure may tend to reclose. Under such circumstances, where the angioplasty has failed it may be necessary to temporarily hold the artery lumen open until the patient can be treated further, possibly by bypass surgery. The guidewire with coil 12 can be advanced into the stenosis to hold the artery open temporarily.

From the foregoing, it will be appreciated that the invention provides a new device and technique for placing a guidewire in a body lumen by causing the guidewire to track along, in monorail fashion, a preexisting indwelling device, such as a catheter or the like. The system enables the guidewire to be placed without loss of position in the patient. It enables quick and effective catheter exchanges, particularly, when it is desired to exchange an integral fixed wire type of catheter for an over-the-wire catheter.

It should be understood, however, that the foregoing description of the invention is intended merely to be illustrative thereof and that other modifications, embodiments, equivalents, may be apparent to those skilled in the art without departing from its spirit.

Having thus described the invention what we desire to claim and secure by Letters Patent is:

1. A guidewire adapted to be received within a lumen of a medical catheter and being further adapted for tracking an indwelling device having a shaft with a proximal end and a distal end, the distal end of the indwelling device being adapted to be positioned within a body lumen, the guidewire comprising:

an elongate, flexible guidewire body having proximal and distal ends;

a tracking member which is selectively movable to engaged and disengaged positions disposed in the region of the distal end of said guidewire body, the tracking member in the engaged position extending transversely of the length of the guidewire and being adapted to receive the shaft of the indwelling device in parallel to the body of the guidewire, said tracking member being slidable along the length of the indwelling device for enabling the guidewire to track the path of the indwelling device, the tracking member in the disengaged position being adapted for release from the shaft of the indwelling device said tracking member including at least one loop which extends radially outwardly from the guidewire body; and means for retracting said loop to draw it radially inwardly to reduce its profile.

2. The guidewire of claim 1 wherein said tracking member is fully removable from the guidewire body.

3. A guidewire for tracking an indwelling device having a shaft with the proximal end and a distal end, the distal end being adapted to be positioned within a body lumen, the guidewire comprising an elongate, flexible guidewire body having proximal and distal ends; and a tracking member disposed in the region of the distal end of said guidewire body and defining an opening adapted to receive the shaft of the indwelling device, said tracking member being slidable in a distal direction along the indwelling device for enabling the guidewire to track the path of the indwelling device;

said tracking member including at least one loop which extends radially outwardly from the guidewire body;

means for retracting said loop to draw it radially inwardly to reduce its profile;

said guidewire body defining a lumen; and said means for retracting including a pull element passing through said lumen, the pull element being accessible at the proximal end of said guidewire body.

4. The guidewire of claim 3 wherein said tracking member is fully removable from the guidewire body.

5. A guidewire adapted to be received within a lumen of a medical catheter and further adapted for tracking an indwelling device having a shaft with a proximal end and a distal end, the distal end of the indwelling device being adapted to be positioned within a body lumen, the guidewire comprising:

an elongate, flexible guidewire body having proximal and distal ends;

a tracking member which is selectively movable to engaged and disengaged positions disposed in the region of the distal end of said guidewire body, the tracking member in the engaged position extending transversely of the length of the guidewire and being adapted to receive the shaft of the indwelling device in parallel to the body of the guidewire, said tracking member being slidable along the length of the indwelling device for enabling the guidewire to track the path of the indwelling device, the tracking member in the disengaged position being released from the shaft of the indwelling device;

said tracking member including at least one loop which extends radially outwardly from the guidewire body; and further including means for withdrawing said loop inside of said guidewire body through an opening defined by said guidewire body.

6. The guidewire of claim 5 wherein said tracking member is fully removable from the guidewire body.

7. A guidewire for tracking an indwelling device having a shaft with a proximal end and a distal end, the distal end being adapted to be positioned within a body lumen, the guidewire comprising an elongate, flexible guidewire body having proximal and distal ends; and a tracking member disposed in the region of the distal end of said guidewire body and defining an opening adapted to receive the shaft of the indwelling device, said tracking member being slidable in a distal direction along the indwelling device for enabling the guidewire to track the path of the indwelling device;

said tracking member being established by the distal end of a wire element which emerges through an opening in said guidewire body and forms a plurality of loops about said guidewire body.

8. The guidewire of claim 7 wherein said tracking member is fully removable from the guidewire body.

9. The guidewire of claim 7 wherein said guidewire body defines a lumen and the proximal end of said wire element extends proximally through said lumen of the guidewire body and emerges from the proximal end of said guidewire body.

10. The guidewire of claim 9 wherein said tracking member is fully removable from the guidewire body.

11. The guidewire of claim 7 wherein a distal portion of said wire element is formed of a metal wire and a proximal portion of said wire element is formed of a component having a greater column strength then the wire.

12. The guidewire of claim 11 wherein said distal portion of said wire element is an alloy of nickel and platinum and said proximal portion includes a silica glass tube.

13. A guidewire adapted to be received within a lumen of a medical catheter and being further adapted for tracking an indwelling device having a proximal end and a distal end positioned within a body lumen, the guidewire comprising:

an elongate tubular shaft having a distal end and a proximal end;

a tubular sleeve having proximal and distal ends and being connected to the distal end of said tubular shaft;

a helical coil spring having proximal and distal ends, being connected to the distal end of said sleeve, and defining an opening proximally of its distal tip;

a wire element emerging transversely through the opening in said coil spring to form a tracking member having at least one loop which is engageable for receiving and is slidable along the outside of the indwelling device for enabling the guidewire to track the path of the indwelling device; and further including means, attached to the proximal end of said wire element, for retracting said tracking member to decrease its profile, said means for retracting extending proximally through said coil spring, said sleeve, and said tubular shaft and being accessible through the proximal end of said shaft.

14. The guidewire of claim 13 in which said wire element is completely removable from said shaft.

15. The guidewire of claim 14 further comprising the proximal end of the guidewire shaft having a connector element adapted to enable an extension wire to be attached to the proximal end of the guidewire shaft thereby to extend the effective length of the guidewire to facilitate a catheter exchange.

16. The guidewire of claim 13 in which said means for retracting includes an elongate element having a greater column strength than said wire element.

17. The guidewire of claim 16 wherein said wire element is an alloy of nickel and platinum and said elongate element is a silica glass tube.

18. A guidewire adapted to be received within a lumen of a medical catheter and being further adapted for tracking an indwelling device having a proximal end and a distal end positioned within a body lumen, the guidewire comprising:

an elongate tubular shaft having a distal end and a proximal end;

a tubular sleeve having proximal and distal ends and being connected to the distal end of said tubular shaft;

a helical coil spring having proximal and distal ends, being connected to the distal end of said sleeve, and defining an opening proximally of its distal tip;

a wire element emerging transversely through the opening in said coil spring to form a tracking member having at least one loop which is engageable for receiving and is slidable along the outside of the indwelling device for enabling the guidewire to track the path of the indwelling device wherein said wire element terminates in a blunt tip and in which said blunt tip is an enlarged, substantially spherical ball.

19. A guidewire adapted to be received within a lumen of a medical catheter and being further adapted for tracking an indwelling device having a proximal end and a distal end positioned within a body lumen, the guidewire comprising:

an elongate tubular shaft having a distal end and a proximal end;

a tubular sleeve having proximal and distal ends and being connected to the distal end of said tubular shaft;

a helical coil spring having proximal and distal ends, being connected to the distal end of said sleeve, and defining an opening proximally of its distal tip;

a wire element emerging transversely through the opening in said coil spring to form a tracking member having at least one loop which is engageable for receiving and is slidable along the outside of the indwelling device for enabling the guidewire to track the path of the indwelling device;

wherein a region of said helical coil spring is expanded to provide a space between the coils of the spring to define the opening through which the wire element emerges.

20. A guidewire adapted to be received within a lumen of a medical catheter and being further adapted for tracking an indwelling device having a proximal end and a distal end positioned within a body lumen, the guidewire comprising:

an elongate tubular shaft having a distal end and a proximal end;

a tubular sleeve having proximal and distal ends and being connected to the distal end of said tubular shaft;

a helical coil spring having proximal and distal ends, being connected to the distal end of said sleeve, and defining an opening proximally of its distal tip;

a wire element emerging transversely through the opening in said coil spring to form a tracking member having at least one loop which is engageable for receiving and is slidable along the outside of the indwelling device for enabling the guidewire to track the path of the indwelling device;

wherein a plurality of coils of said helical coil spring are expanded to provide gaps between the coils in an expanded region, the wire element forming a plurality of loops about said coil spring, and the expanded region being at least as long as the length of said tracking member loops.

21. The guidewire of claim 20 wherein one side of said tracking member loops is slidable through the expanded coils to increase the effective inner diameter of said tracking member and to interlock said tracking member with the expanded coils to inhibit longitudinal movement between them.

22. A guidewire, of a type insertable in a guidewire lumen of an over-the-wire catheter, for tracking an elongate indwelling device having a shaft with a proximal end and a distal end positioned within a body lumen, the guidewire comprising:

a guidewire body having proximal and distal ends;

a tracking member disposed at the distal region of said guidewire body, means for configuring the tracking member alternately in a first expanded configuration defining an opening passable over the shaft of the indwelling device thereby to enable said tracking member to track the path of the indwelling device and a second, contracted configuration for enabling an over-the-wire catheter to be guided along said path by following along the guidewire.

23. A method of tracking an indwelling device having a shaft with a proximal portion exposed externally of a patient's body and a distal end positioned at a selected site within a body lumen, comprising:

providing a guidewire adapted to be received within the lumen of a medical catheter, the guidewire having a guidewire body and a retractable tracking member disposed at the region of the distal end of the guidewire body;

passing the exposed proximal portion of the shaft of the indwelling device through the retractable tracking member;

advancing the guidewire into the body lumen, the tracking member sliding along the indwelling device towards its distal end to enable the guidewire to track the path of the indwelling device;

withdrawing the indwelling device after the distal end of the guidewire is positioned at the selected site;

further including retracting the retractable tracking member to decrease its profile after the tracking member is positioned distally relative to the distal end of the indwelling device.

24. The method of claim 23 further including advancing an over-the-wire catheter over the guidewire to position the balloon within the stenosis.

25. The method of claim 24 further comprising:

before passing the over-the-wire catheter over the guidewire, attaching an extension wire to the proximal end of the guidewire, the extension wire being of a length such that the total exposed length of the extension wire and guidewire is greater than the length of the over-the-wire catheter; and during advancement of the over-the-wire catheter, maintaining the position of the guidewire by holding the exposed portion of the guidewire or guidewire extension.

26. A method as defined in claim 24 wherein the length of the guidewire is such that when the distal end of the guidewire is positioned at the selected site, the length of the guidewire that extends proximally and exteriorly of the patient will be greater than the length of the over-the-wire catheter.

27. The method as defined in claim 24 wherein said catheter comprises a balloon dilatation catheter.

28. A guidewire adapted to be received within a lumen of a medical catheter and further adapted for tracking an indwelling device having a shaft with a proximal end and a distal end, the distal end of the indwelling device being adapted to be positioned within a body lumen, the guidewire comprising:

an elongate, flexible guidewire body having proximal and distal ends; and a tracking member which is selectively movable to engaged and disengaged positions disposed in the region of the distal end of said guidewire body, the tracking member in the engaged position extending transversely of the length of the guidewire and being adapted to receive the shaft of the indwelling device in parallel to the body of the guidewire, said tracking member being slidable along the length of the indwelling device for enabling the guidewire to track the path of the indwelling device, the tracking member in the disengaged position being released from the shaft of the indwelling device wherein said tracking member is fully removable from the guidewire body.

29. A guidewire adapted to be received within a lumen of a medical catheter and further adapted for tracking an indwelling device having a shaft with a proximal end and a distal end, the distal end of the indwelling device being adapted to be positioned within a body lumen, the guidewire comprising:

an elongate, flexible guidewire body having proximal and distal ends;

a tracking member which is selectively movable to engaged and disengaged positions disposed in the region of the distal end of said guidewire body, the tracking member in the engaged position extending transversely of the length of the guidewire and being adapted to receive the shaft of the indwelling device in parallel to the body of the guidewire, said tracking member being slidable along the length of the indwelling device for enabling the guidewire to track the path of the indwelling device, the tracking member in the disengaged position being released from the shaft of the indwelling device;

wherein said tracking member includes at least one loop which extends radially outwardly from the guidewire body and wherein said tracking member is fully removable from the guidewire body.

30. A guidewire adapted to be received within a lumen of a medical catheter and further adapted for tracking an indwelling device having a shaft with a proximal end and a distal end, the distal end of the indwelling device being adapted to be positioned within a body lumen, the guidewire comprising:

an elongate, flexible guidewire body having proximal and distal ends;

a tracking member which is selectively movable to engaged and disengaged positions disposed in the region of the distal end of said guidewire body, the tracking member in the engaged position extending transversely of the length of the guidewire and being adapted to receive the shaft of the indwelling device in parallel to the body of the guidewire, said tracking member being slidable along the length of the indwelling device for enabling the guidewire to track the path of the indwelling device, the tracking member in the disengaged position being released from the shaft of the indwelling device, wherein said tracking member includes at least one loop which extends radially outwardly from the guidewire body, wherein said loop is formed of a wire, and wherein said tracking member is fully removable from the guidewire body.

* * * * *